United States Patent [19]

Friemel et al.

[11] Patent Number: 4,720,380

[45] Date of Patent: * Jan. 19, 1988

[54] HYDROGEN-PHOSPHIDE RELEASING COMPOSITIONS AND PROCESSES FOR THEIR PRODUCTION AND USE

[75] Inventors: Wolfgang Friemel, Heppenheim; Reiner Ehret, Weinheim, both of Fed. Rep. of Germany

[73] Assignee: Dr. Werner Freyberg Chemische Febrik Delitia Naschf., Laudenbach, Fed. Rep. of Germany

[ * ] Notice: The portion of the term of this patent subsequent to Mar. 5, 2002 has been disclaimed.

[21] Appl. No.: 720,900

[22] Filed: Mar. 4, 1985

Related U.S. Application Data

[63] Continuation-in-part of Ser. No. 436,769, Oct. 26, 1982, Pat. No. 4,503,032, which is a continuation of Ser. No. 215,586, Dec. 11, 1980, abandoned.

[30] Foreign Application Priority Data

Dec. 18, 1979 [DE] Fed. Rep. of Germany ....... 2950999

[51] Int. Cl.$^4$ ................... A01N 59/16; A01N 59/26; A01N 25/18
[52] U.S. Cl. .................................... 424/40; 424/128; 424/145

[58] Field of Search .................. 424/40, 128, 145

[56] References Cited

U.S. PATENT DOCUMENTS

| | | | |
|---|---|---|---|
| 2,826,486 | 3/1958 | Hiiter | 424/128 |
| 3,132,067 | 5/1964 | Rauscher et al. | 424/128 |
| 3,372,088 | 3/1986 | Freyberg et al. | 424/128 |
| 3,917,823 | 11/1975 | Kapp | 424/128 |
| 4,213,967 | 7/1980 | Praxl et al. | 424/128 |
| 4,376,112 | 3/1983 | Miller | 424/128 |
| 4,503,032 | 3/1985 | Friemel et al. | 424/40 |

FOREIGN PATENT DOCUMENTS

| | | |
|---|---|---|
| 1143053 | 1/1963 | Fed. Rep. of Germany . |
| 1569514 | 6/1983 | United Kingdom . |

*Primary Examiner*—J. R. Brown
*Assistant Examiner*—F. T. Moezie
*Attorney, Agent, or Firm*—Millen & White

[57] ABSTRACT

The likelihood of auto-ignition occurring while hydrolyzing particulate aluminum phosphide with $H_2O$ to produce phosphine is reduced by conducting the hydrolysis of the aluminum phosphide in the presence of both a source of ammonia or ammonium ions and zinc or zinc compound, the latter reducing the temperature rise associated with the hydrolysis.

19 Claims, No Drawings

HYDROGEN-PHOSPHIDE RELEASING COMPOSITIONS AND PROCESSES FOR THEIR PRODUCTION AND USE

This is a continuation-in-part of Application Ser. No. 436,769, now U.S. Pat. No. 4,503,032, filed Oct. 26, 1982 as a continuation of Application Ser. No. 215,586, filed Dec. 11, 1980, now abandoned.

BACKGROUND OF THE INVENTION

The present invention relates to hydrogen phosphide-releasing compositions, especially to pest control agents, comprising aluminium phosphide.

For purposes of pest control and protection of stored agricultural commodities preparations based on hydrolysable phosphides of alkaline earth and/or earth metals such as calcium, magnesium or aluminium phosphide are employed to an increasing extent. These are caused by atmospheric humidity or the moisture content of stored commodities to decompose into highly toxic phosphine and inert oxides/hydroxides. The liberated phosphine may auto-ignite under certain unfavorable conditions, for which reason special expedients are necessary to permit the application safely and without hazard. In addition it is generally desired to so regulate the hydrolysis rate of the phosphides that the fumigation workers are not exposed unnecessarily to toxic gas concentrations.

Substances which thermally decompose to liberate $NH_3$ and/or $CO_2$ such as ammonium bicarbonate, ammonium carbonate, ammonium carbamate etc. have been used successfully for suppressing the tendency to auto-ignite of phosphine formed hydrolytically from phosphides. More recently other inhibitors have been described which even in low concentrations inhibit or retard the spontaneous reaction between phospine and atmospheric oxygen. It is also known to admix to the phosphide readily volatile organic substances, the heat of evaporation of which causes the phosphide particles to be surrounded by a cooled zone, thereby preventing heat accumulation which might result in ignition of the phosphine.

These measures have very little or no effect on the violent rate of formation of the phosphine which results when the metal phosphide comes into contact with liquid water. To suppress this reaction with liquid water it has been proposed to hydrophobise the phosphides or phosphide particles. Paraffins, waxes, stearates, silicones, synthetic resins etc. have been described as hydrophobing agents. See, e.g., U.S. Pat. No. 3,132,067; 3,372,088; Fed. Rep. of Germany DOS 27 05 228; and U.S. Application Ser. No. 964,410, filed Nov. 28, 1978, now abandoned, whose disclosure is incorporated herein by reference, and the references cited therein. It is also known that the individual phosphide particles or groups of particles are coated with a water-repellent dense coating which is claimed to prevent hydrolysis such that a bursting substance is added which is said to burst open the coating and thus trigger the reaction with moisture after a time delay.

It was furthermore known to depress the reactivity of metal phosphides against liquid water in pest control; agents by blocking the hydrophilic centers of the phosphides with water-insoluble metal soaps, in particular stearates. The expressly described purpose of this procedure was the abolition of previously known auto-ignition inhibitors, in particular ammonia salts such as ammonium carbamate. This procedure was equally effective for calcium phosphide, magnesium phosphide as well as aluminium phosphide. For various commercial and practical reasons aluminium stearate (and to a lesser extent magnesium stearate) were selected as the preferred blocking agent and even used on a commercial scale in certain countries by the present applicant.

Practical experience and experiments have shown that the above described teaching may at the most serve to maintain a reasonable control over the hydrolysis of alkaline earth and earth metal phosphides caused by atmospheric humidity. If phosphide containing pest control agents prepared according to the state of the art, are contacted with liquid water, as may very well happen accidentally in practice, it is found that, depending on the ratio of water/preparation more or less severe steam generation and temperature rises to values even exceeding 100° C. may result, demonstrating that the reaction cannot be controlled adequately. Under such conditions the admixed protecting agents are volatilised very rapidly so that they do not yield an adequate protective effect. Moreover, the measured reaction temperatures are at least in part within the range of the ignition temperature of phosphine which according to the literature is approximately 100° C. In the experiments, the oxidation of the phosphine, i.e., the formation of $P_2O_5$, smoke and sometimes even spontaneous ignition may be observed. It would be highly desirable—and this is an object of this invention—to mitigate this safety risk which should not be underestimated in the practical context, and nevertheless to provide an easily manufactured and safely applied pest control agent based on hydrolyzable aluminium phosphide.

SUMMARY OF THE INVENTION

The present invention relates to a method for reducing the likelihood of auto-ignition occurring while hydrolyzing particulate aluminum phosphide by conducting type hydrolysis of the aluminum phosphide in the presence of both a source of ammonia or ammonium ions and zinc or zinc compound, the latter reducing the temperature rise associated with the hydrolysis.

DETAILED DISCUSSION

The hydrogen phosphide releasing agent preferably comprises the aluminium phosphide in finely particulate form, intimately mixed with the remaining ingredients of the aforesaid combination.

The composition which optionally contains conventional additives can be advantageously used as a pest control agent.

In that case the composition may be made up in a conventional manner for that purpose, e.g. in the form of pellets, tablets or sachets (filled with the composition in powder or granulate form) representing standardised dosage units as conventionally used in the art, e.g. for the direct application of warehouses, siols, storage bins or similar closed spaces containing, e.g., agricultural commodities or for the control of burrowing animals. The procedure suitable for pest control using the claimed compositions can be the same as are normally employed with prior art compositions.

As would be apparent to those skilled in the art, the aluminum phosphide need be in admixture with the source of ammonia or of ammonium ions and with the zinc or zinc compound only at the moment of contact of the aluminum phosphide with the $H_2O$ in order for them to manifest their auto-ignition inhibiting effect. Therefore, in a method aspect, the aluminum phosphide is brought in contact with one or both of the source of ammonia or ammonium ions and the zinc or zinc compound substantially simultaneously with being exposed to $H_2O$ in vapor or liquid form, e.g., by hydrolyzing the aluminum phosphides as an intimate admixture with the zinc or zinc compound, with liquid water containing the source of ammonia or ammonium ions dissolved therein.

It was found that the decomposition of this pest control agent in accordance with the invention brought about by liquid water proceeds extremely slowly. In the hydrolysis experiments conducted not a single case of steam or, even worse, $P_2O_5$ formation was observed and the maximum reaction temperatures were in the region of 50° C. Moreover, it made little or no difference whether the formulations were used in loose or compacted form.

Not even the ratio of the preparation to water had any serious influence on the progress of the hydrolysis. However, the decomposition of formulations according to the invention brought about by atmospheric moisture, i.e. the gas generating characteristics are not affected by the addition of the zinc compounds.

Accordingly, it was found possible for the first time to prevent reliably in the case of an aluminium phosphide containing pest control agent the ignition temperature being even approached. This provides protection against an ignition of the hyrogen phosphide taking place even when liquid water is permitted to contact the pest control agent, e.g., due to careless use or malpractice.

Surprisingly, not only metallic zinc in powder form and zinc oxide, but also salt-like zinc compounds which contain zinc cations are effective to inhibit hydrolysis. The nature of the anion was found to be immaterial, although obviously a person skilled in the art would avoid anions which are strong oxidising agents or which in the context of practical use are likely to produce undesirable corrosion or toxicity problems, e.g., in the residue from the spent preparations. Preferably the quantities employed amount to about 0.1–5% by weight of the composition, which composition comprises aluminium phosphide, an $NH_3$ or $[NH_4]^+$ generating substance and, where appropriate, an hydrophobing agent. Higher proportions are possible, but do not result in any further improvement. In selecting a suitable zinc compound care should obviously be taken to ensure that it is anhydrous and will not adversely affect the physical and chemical characteristics of the phosphide. Zinc oxide, inorganic salts of zinc and weak or strong mono or polybasic acids, e.g. basic zinc carbonate, zinc sulphate or zinc borate, and organic zinc salts, e.g., salts of organic fatty acids, e.g. zinc soaps, especially zinc stearate, are particularly suitable. These zinc compounds are advantageously employed in finely comminuted form; their effectiveness increases as the specific surface thereof is increased.

Essential for an inventive effect of the zinc compounds is the presence in the composition of a source of ammonia or ammonium ions, e.g., a substance which is decomposable under conditions under which the aluminium phosphide is hydrolyzed to yield $NH_3$, e.g. thermally, such as for example, ammonium bicarbonate, ammonium carbonate, ammonium carbamate, or which is capable of dissociating, e.g. in the presence of water, to yield ammonium ions, e.g. ammonium biphosphate and ammonium chloride, etc. If such a substance is lacking, the zinc compounds lack the desired effect. The amount of added substance yielding $NH_3$ or $[NH_4]^+$ is in the range of 10 to 50%, preferably 15 to 30% based on the total amount of the composition. Appreciable variations above this range can be tolerated. Substances which yield $NH_3$ by decomposition are of course also sources of ammonium ion in the presence of liquid water. Apparently the ammonium ion (in a manner not yet understood), plays a part in the protective mechanism which suppresses violent reactions with liquid water. Surprisingly, the zinc compounds or the metallic zinc only influence the hydrolytic reaction of aluminium phosphide with water and they exert this influence only if ammonia or ammonium ion generating compounds are present. The reaction of other metal phosphides conventionally employed in pest control, namely magnesium and calcium phosphide, is not affected to any material extent. It is a further surprising fact that the hydrolysis retarding effect of the zinc compounds or zinc powder is observed even in the absence of the normally used hydrophobing agents. However, since conventional hydrophobing agents, such as for example, paraffins, waxes, stearates, etc. besides their hydrophobic effect also act as lubricants and binding agents in the context of making compressed bodies, their use in making compacted pest control compositions of this invention is advantageous.

The aluminium phosphide can be, and in practice generally will be, of a technical grade as is produced in a kiln by reaction of pure aluminium powder with red phosphorus. The product, hereinafter referred to as technical aluminium phosphide, is substantially composed of aluminium phosphide and aluminium oxide. The AlP content is preferably about 75 to 90%, more particularly 85%

The technical aluminium phosphide is ground to a powder composed of particles ranging from fine dust up to $2000\mu$, preferably not more than 20% being larger than $1000\mu$ or smaller than $50\mu$.

When it is desired to achieve a good granulation effect without impairing the wettability of the composition, e.g. for purposes of complete hydrolysis of spent residues of such compositions, a water-soluble non-water repellent polymer is preferred.

The protective effect afforded by the combination of zinc (or zinc compound) and ammonia and/or ammonium ion on the aluminium phosphide is so great that for the first time it is now possible even to intentionally contact the aluminium phosphide composition with liquid water, e.g. for the purpose of generating phosphine gas substantially free of the higher homologues of phosphine, e.g. for laboratory or other chemical use or for pest control purposes.

Accordingly, the present invention according to one of its aspects also provides a use of the composition as set out herein, namely a method of generating phosphine gas which comprises exposing a composition as herein set out, to water, thereby hydrolysing the aluminium phosphide with the formation of phosphine gas. The water may be in vapor form (as in prior art fumigation methods employing metal phosphide preparations) or it may be employed in liquid form, e.g. in a generator vessel which can be of quite simple construction.

For pest control purposes, the phosphine gas generated may be introduced immediately into and maintained in an environment infested with pests to be eradicated.

To be on the safe side even under extreme conditions, it is sometimes advantageous to add to the pest control agent small quantities of other ignition inhibiting substances, many of which are known in the prior art, e.g., certain alkyl and alkenyl substituted aromatic hydrocarbons having, e.g., a benzene nucleus substituted with 2-5 alkyl or alkenyl substituents or a naphthalene nucleus substituted with 2-3 alkyl or alkenyl substituents can be used. See, e.g., U.S. Pat. No. 4,213,967, whose disclosure is incorporated herein by reference.

Further precautions in the context of hydrolysing the preparations with liquid water are directed to minimizing heat build-up. For this purpose the aluminium phosphide composition in granulate, pellet or tablet form is fed little by little into a generating vessel containing water, e.g. with known metering devices, preferably over a period spread out over a major part of the total fumigation period. This procedure (which can be fully automated in manners requiring no detailed description) can simultaneously serve to maintain in the space a phosphine concentration range known to be optimum for the particular fumigation procedure (which may vary depending on climate, nature of the pests, nature of the commodity, nature of the space and time available for the fumigation).

In the context of fumigating a warehouse, silo, storage bin or similar closed space, e.g. containing agricultural commodities to be fumigated, the air may be withdrawn by suction from such space into a phosphine generating vessel and recycled, together with phosphine into the space. The recycling may take place through one or more pipes which preferably extend some distance away from the walls into the space interior.

If comparatively large quantities of the composition have to be hydrolysed in a relatively short time it may be advisable to subject the water in the generator vessel to cooling.

The following examples serve to elucidate the invention without limiting the same. All proportions, unless otherwise stated, are given in parts by weight (mass). The technical aluminium phosphide used in the examples is of conventional grade (85% AlP), ground to a powder substantially in the particle range 50–200 µ and typically having the following particle size distribution:

>1000µ 10%
>500µ 30%
>100µ 85%
<100µ 15% and a loose bulk density of 0.7 g/cm³.

EXAMPLE 1

70 parts technical aluminium phosphide, 25 parts ammonium carbamate and 3 parts stearin were intimately mixed. The basic mixture was divided, one half being pressed directly into moulded bodies of 3 g each, the other half being similarly pressed after the admixture thereto of 2% of a commercial grade of zinc stearate having a bulk density after shaking of 115 g/l. Lots of 10 tablets each of each composition were subjected in a 250 ml glass beaker to a drenching with 30 ml H₂O at 20° C. The temperature rise caused by the hydrolysis was measured by means of an electrical thermometer.

Whereas the temperature maximum of the formulation containing zinc stearate was about 37° C., the basic mixture attained a maximum value of about 93° C.

EXAMPLE 2

70 parts technical aluminium phosphide were mixed at 120° C. with 4 parts hard paraffin according to DAB 6.* After cooling to room temperature the hydrophobised AlP was mixed with 26 parts ammonium carbamate and one half of this mixture was pressed directly into moulded bodies of 3 g each (A). The other half of the mixture was similarly pressed to tablets of 3 g each, after the addition thereto of 0.5 parts of a zinc oxide having a BET surface area of 10 m²/g. Subsequently all moulded bodies were subjected to a brief thermal treatment (1 hour, 70 degrees C. in a closed vessel) to increase the hydrophobic effect.
* German Pharmacopeia Vol. 6

Lots of 10 tablets each of each composition were hydrolized in a 400 ml glass beaker with 30 ml H₂O. In the case of the formulation according to the invention, the maximum reaction temperature was about 31° C., while the tablets without zinc oxide attained 105° C. In the latter case P₂O₅ smoke was observed.

EXAMPLE 3

60 parts technical aluminium phosphide, 35 parts urea and 3 parts aluminium stearate were intimately mixed with 10 parts of a 20% suspension of zinc stearate according to example 1 in dichloromethane (B). A second mixture was produced in which the 20 parts urea were replaced by ammonium carbamate. The mixture containing ammonium carbamate during the hydrolysis experienced only very moderate reaction, whilst the phosphine formed by the hydrolysis from the other formulation ignited spontaneously. The reaction temperature measured prior to the ignition reached about 107° C.

EXAMPLE 4

70 Parts technical aluminium phosphide were treated at 140° C. for one hour with 0.5 parts of a methyl hydrogen polysiloxane in the absence of air. After the silicone had been cured and after cooling to room temperature 15 parts ammonium chloride and 14 parts urea and 0.5 parts finely comminuted zinc borate were added.

Lots respectively composed of 10 tablets of 3 n pressed from this mixture and 10 tablets of a mixture of 70 parts technical aluminium phosphide, 26 parts ammonium carbamate and 4 parts hard paraffin DAB 6 were drenched at 35° C. room temperature in a 250 ml glass beaker with 30 ml H₂O at 35° C. The maximum reaction temperature in the case of the formulation according to the invention was about 39° C. The control tablets attained a maximum value of 92° C. with steam development.

EXAMPLE 5

Batches of 10 each of the tablets according to the invention and of the control tablets according to example 4 were exposed to air for 3 hours. This was followed by a hydrolysis experiment as in example 4. The tablets according to the invention reacted very slowly and attained a maximum reaction temperature of 38° C. The phosphine gas evolved by the control tablets achieved auto-ignition after a brief reaction period.

EXAMPLE 6

A mixture of 70 parts technical phosphide, 15 parts ammonium chloride, 14.8 parts urea and 0.2 parts of a zinc oxide according to example 2 were pressed into pellets of 0.6 g each. 50 g of these tablets were subjected to reaction in a 1 liter beaker with 50 ml H2O. The hydrolysis proceeded extremely slowly and the maximum reaction temperature was about 23° C.

Tablets were hydrolyzed as a control which had the same composition except that they contained no zinc oxide (C). Shortly after the start of the hydrolysis, the phosphine generated ignited.

EXAMPLE 7

70.5 parts of an aluminium phosphide treated in accordance with example 4, 19.3 parts urea, 10 parts ammonium carbamate and 0.2 parts zinc oxide (BCT surface area 10 m² g) were mixed intimately in the absence of air and subsequently pressed into tablets of 3 g each.

Tablets were used as a control which were composed of a mixture of 70.5 parts siliconised aluminium phosphide, 19.5 parts urea and 10 parts ammonium carbamate. (D). 10 tablets of each batch were hydrolysed in a 250 ml glass beaker with 30 ml H₂O. The reaction temperature of the formulation containing zinc oxide attained a maximum temperature of 35° C. The control tablets attained 105° C. with a formation of P₂O₅ smoke.

EXAMPLE 8

70 parts technical aluminium phosphide, 15 parts ammonium carbamate, 13.5 parts urea, 0.5 parts zinc oxide were mixed intimately and subsequently sprayed with 10 parts of a 10% solution of polyvinyl pyrrolidone in dichloromethane. After the evaporation of the solvent, the formulation took the form of a fine granulate. 50 g each of this granulate and of an otherwise identical granulate lacking the omission of the zinc oxide were subjected to reaction with 50 ml H₂O in a 400 ml glass beaker.

The reaction of the granulate without zinc oxide proceeded rapidly and violently with the formation of P₂O₅ smoke. The formulation in accordance with the invention reacted very slowly and only attained a maximum reaction temperature of 37° C. in spite of the absence of any hydrophobing agent.

EXAMPLE 9

70 parts technical aluminium phosphide, 20 parts ammonium carbamate, 7 parts urea and 3 parts aluminium stearate were intimately mixed in the absence of air.

This mixture was divided, one half being pressed directly into moulded bodies of 3 g each, and the other half was so pressed after the addition of two parts zinc powder (commercially known as Zn dust).

These pressed tablets were subjected to the following hydrolysis tests: batches of 10 tablets were each drenched in a 400 ml glass beaker with 20 ml water and the temperature rise during the hydrolysis was measured. The temperature maximum of the zinc containing tablets was in the region of 34° C., whereas the tablets without zinc attained 94° C. and formed P₂O₅ smoke.

EXAMPLE 10

70 parts of a technical aluminium phosphide, 15 parts ammonium carbamate, 12 parts urea and 3 parts stearic acid were intimately mixed in the absence of air. One half thereof was directly pressed into tablets of 6 g each and the other half was so pressed after the addition of 2 parts zinc sulphate.

A hydrolysis experiment (according to example 9) was then conducted, in which the reaction of the pest control bodies containing zinc sulphate proceeded very gently, the maximum temperature being at 33° C. The control pressed bodies reacted considerably more violently with the formulation of P₂O₅ smoke.

EXAMPLE 11

Tablets were produced according to example 10 in which the zinc sulphate was replaced by basic zinc carbonate.

These tablets reacted very slowly with H₂O, whereas the corresponding tablets free of zinc salt experienced a violent reaction and evolved P₂O₅ smoke.

TABLE 1

| Formulation according to example | Composition in parts by weight | Temperature after | | | | | T max. (min) |
|---|---|---|---|---|---|---|---|
| | | 5 min | 10 min | 15 min | 30 min | 60 min | |
| 1 | 70 AlP, 25 AC, 3 stearin, 2 Zn—stearate | 22 | 24 | 26 | 34 | 32 | 37° (55 min) |
| 2 | 70 AlP, 26 AC, 4 Paraffin 0.5 ZnO | 22 | 23 | 25 | 27,5 | 28 | 31° (95 min) |
| 3 | 60 AlP, 20 AC, 15 urea, 3 Al stearate, 2 Zn stearate | 21 | 23,5 | 26 | 29 | 34 | 36° (45 min) |
| 4 | 70 AlP, 15 NH₄Cl, 14 urea, 0.5 H—siloxane, 0.5 Zn—borate | 21 | 22 | 23,5 | 26 | 26,5 | 26,5° (55 min) |
| 6 | 70 AlP, 15 NH₄Cl, 14.8 urea, 0.2 ZnO | 20 | 20 | 20,5 | 21,5 | 22 | 23° (75 min) |
| 7 | 70 AlP, 10 AC, 19.3 urea, 0.5 H—siloxane, 0.2 ZnO | 22 | 24 | 27 | 33 | 34 | 35° (75 min) |

AlP = aluminum phosphide of technical grade
AC = ammonium carbamate

| Control Batch | Composition in parts by weight | Temperature after | | | | T max. (min) |
|---|---|---|---|---|---|---|
| | | 5 min | 10 min | 15 min | 30 min | |
| A | 70 AlP, 26 AC, 4 Paraffin | 25 | 31 | 62 | 80 | 105° (20 min) |
| B | 60 AlP, 35 urea, 3 Al—stearate 2 Zn—stearate | 25 | 43 | 104 | | 107° (17 min) |
| C | 70 AlP, 15 NH₄Cl, 15 urea | 28 | 74 | 97 | | 114° (13 min) |
| D | 70 AlP, 10 AC, 19.5 urea, 0.5 H—siloxane | 26 | 37 | 63 | 76 | 105° (24 min) |

AlP-technical aluminum phosphide, AC-ammonium carbonate, paraffin: hard paraffin DAB 6 H—siloxane - hydrogenpolymethylsiloxane The tablets according to examples 1 to 6 were subjected to the following experiment:

3 tablets each were exposed in a gas chamber of ½ m² capacity at 20° C. and approximately 70% relative air humidity, and the amount of PH₃ liberated was determined by means of Draeger tubes at fixed intervals. It was found that in spite of extremely retarded reaction with liquid water, the reaction with atmospheric moisture was not impeded.

The results are tabulated in table 2. The samples are denoted as in table 1.

TABLE 2

| Formulation according to example | PH₃ generation | | | | | | | |
|---|---|---|---|---|---|---|---|---|
| | 30 min | 1 h | 2 h | 3 h | 4 h | 5 h | 6 h | 24 h |
| 1 | 80 | 120 | 240 | 370 | 490 | 560 | 680 | 2400 |
| 2 | 80 | 180 | 280 | 320 | 400 | 540 | 680 | 2350 |
| 3 | 40 | 90 | 180 | 290 | 370 | 510 | 610 | 2400 |
| 4 | 60 | 160 | 280 | 430 | 600 | 670 | 790 | 2350 |
| 6 | 90 | 200 | 300 | 450 | 550 | 700 | 790 | 2400 |
| A | 70 | 180 | 250 | 350 | 400 | 520 | 700 | 2400 |
| B | 80 | 180 | 270 | 350 | 410 | 500 | 590 | 2200 |
| C | 90 | 190 | 310 | 450 | 630 | 710 | 780 | 2350 |

Table 2 shows clearly that the addition of the zinc compounds in accordance with the invention does not interfere with the decomposition of the aluminium phosphide due to atmospheric moisture. In this context it should be noted that the formulation according to example 3 contains 60% aluminium phosphide.

The present invention makes possible the provision of pest control agents on the basis of hydrolyzable aluminium phosphide which while retaining the desired gas generation characteristics in accordance with the existing state of the art, contributes substantially to improved safety against fire in the practical application of these pest control agents.

What is claimed is:

1. A method of reducing the risk of auto-ignition of particulate aluminum phosphide by contact with liquid water while generating phosphine therefrom by hydrolysis thereof with H₂O, which comprises conducting the hydrolysis while the aluminum phosphide is in contact with (a) a source of ammonia or ammonium ions which is decomposable to yield NH₃ under conditions under which the aluminum phosphide is hydrolyzed or which is capable of dissociating in the presence of H₂O to yield ammonium ions, in an amount effective to inhibit auto-ignition of the aluminum phosphide in the presence of humidity; and (b) zinc or a zinc compound which is compatible with the aluminum phosphide, in an amount effective to reduce the temperature rise associated with the hydrolysis of the aluminum phosphide with liquid water while in contact with the source of ammonia or ammonium ions, thereby further reducing the likelihood of auto-ignition of the aluminum phosphide upon contact with liquid water.

2. A method according to claim 1 wherein the aluminum phosphide is hydrolyzed with H₂O in the form of water vapor.

3. A method according to claim 2 wherein the aluminum phosphide is exposed to the water vapor in an environment susceptible to infestation by pests.

4. A method according to claim 1 wherein the aluminum phosphide is hydrolyzed with H₂O in the form of liquid water.

5. A method according to claim 4 wherein the phosphine gas thus produced is introduced into and maintained by an environment susceptible to infestation by pests.

6. A method according to claim 1 wherein the aluminum phosphide is in contact with an organic zinc compound.

7. A method according to claim 6 wherein the zinc compound is a zinc soap.

8. A method according to claim 7 wherein the zinc soap is zinc stearate.

9. A method according to claim 1 wherein the aluminum phosphide is in contact with an inorganic zinc compound.

10. A method according to claim 9 wherein the inorganic zinc compound is zinc oxide.

11. A method according to claim 9 wherein the inorganic zinc compound is zinc hydroxide-carbonate, zinc sulfate or zinc borate.

12. A method according to claim 1 containing metallic zinc powder.

13. A method according to claim 1 wherein the source of ammonia or ammonium ion is an ammonium salt.

14. A method according to claim 1 wherein the aluminum phosphide is in intimate admixture with a hydrophobing agent.

15. A method according to claim 1 wherein the aluminum phosphide is in intimate contact with at least about 0.1% by weight of the zinc or zinc compound, based on the combined weight of (a), (b) and the aluminum phosphide.

16. A method according to claim 15 wherein the amount of the zinc or zinc compound is 0.2 to 3% by weight.

17. A method according to claim 16 wherein the aluminum phosphide is in intimate contact with at least about 10% by weight of the source of ammonia or ammonium ion, based on the combined weight of (a), (b) and the aluminum phosphide.

18. A method according to claim 17 wherein the amount of the source of ammonia or ammonium ion is 15 to 30% by weight.

19. A method according to claim 1 wherein the amount of technical grade aluminum phosphide which is hydrolyzed is about 30 to 75% by weight, based on the combined weight of (a), (b) and the aluminum phosphide.

* * * * *